(12) United States Patent
Kasch et al.

(10) Patent No.: US 6,339,079 B1
(45) Date of Patent: Jan. 15, 2002

(54) STEROID SULFAMATES, METHOD FOR THE PRODUCTION AND USE THEREOF

(75) Inventors: Helmut Kasch; Winfried Schumann, both of Jena; Johannes Roemer, Grosserkmannsdorf; Joerg Steinbach, Dresden, all of (DE)

(73) Assignee: id pharma GmbH, Jena (DE)

( * ) Notice: Subject to any disclaimer, the term of this patent is extended or adjusted under 35 U.S.C. 154(b) by 0 days.

(21) Appl. No.: 09/381,708

(22) PCT Filed: Mar. 18, 1998

(86) PCT No.: PCT/DE98/00813

§ 371 Date: Feb. 2, 2000

§ 102(e) Date: Feb. 2, 2000

(87) PCT Pub. No.: WO98/42729

PCT Pub. Date: Oct. 1, 1998

(30) Foreign Application Priority Data

Mar. 25, 1997 (DE) .......................... 197 12 488

(51) Int. Cl.$^7$ .......................... A01N 45/00; C07J 31/00; C07J 41/00

(52) U.S. Cl. .......................... 514/182; 514/26; 552/626

(58) Field of Search .................... 514/26, 182; 552/626

(56) References Cited

U.S. PATENT DOCUMENTS

| 3,951,958 A | 4/1976 | Prezewowsky et al. .. 260/239.5 |
| 3,951,959 A | 4/1976 | Prezewowsky et al. 260/239.55 |

FOREIGN PATENT DOCUMENTS

| DE | 24 26 777 | 12/1975 |
| DE | 44 29 397 | 2/1996 |
| DE | 44 29 398 | 2/1996 |
| DE | 195 40 233 | 4/1997 |
| DE | 195 48 449 | 6/1997 |
| WO | WO 96/05216 | 2/1996 |

*Primary Examiner*—Sreeni Padmanabhan
(74) *Attorney, Agent, or Firm*—Reed Smith LLP

(57) ABSTRACT

A novel class of gonane type and D-homo-gonane type steroids having sulfatase-inhibiting and/or estrogenic activity is presented for application in the pharmaceutical industry. The number and location of sulfamoyloxy groups on the steroids provides for sulfatase inhibiting and estrogenic activities that independently vary over a wide range, allowing the customization of the pharmaceutical for specific purposes, including treatment and diagnosis of estrogen-dependent tumors.

9 Claims, No Drawings

STEROID SULFAMATES, METHOD FOR THE PRODUCTION AND USE THEREOF

This application is a 371 of PCT/DE98/00813 filed Mar. 18, 1998.

BACKGROUND OF THE INVENTION a) Field of the Invention

The present invention is directed to gonane type and D-homogonane type steroids with a sulfatase-inhibiting and/or estrogenic activity for application in pharmacological research and in the pharmaceutical industry.

b) Description of the Related Art

Steroid-3-sulfamates with a sultamoyloxy group, alkyl group, cycloalkyl group or dialkylsulfamoyloxy group have long been known (DE 3376799, 1968, Schwarz, S., *Pharmazie* 30 (1975) 17–21). Due to their improved bioavailability and decreased metabolic degradation per hepatic passage, they are used as prodrugs for estrogens in substitution therapy, in the form of combination preparations for contraception, and as substances with scavenging properties.

In steroid sulfamates (DE 2,336,431), only 1,3-dialkylsulfamoyloxy-8α-estratien-17-on as well as certain, possibly substituted, 3,11- and 3,17-disulfamoyloxy estratiens, which are used especially as hormonal contraceptives (WO 96/05216), are identified as likewise having an estrogenic activity. Recently, it was found by M. J. Reed, et al. [*Biochemistry* 34 (1995) 11508–11514; *J. Steroid Biochem. Molec. Biol.* 57 (1996) 79–88] that a strong sulfatase-inhibiting activity is exerted by estradiol- and estrone-3-sulfamates. Sulfatase inhibitors can be used to treat estrogen-dependent tumors in that they prevent the release of estradiol or estrone from endogenic steroid conjugates, i.e., the corresponding sulfates. It was subsequently indicated that steroidal sulfatase inhibitors of the estradiol- or estrone-3-sulfamate type can be used only conditionally as sulfatase inhibitors for treating estrogen-dependent tumors. In in vivo experiments, these compounds show an increased estrogenic activity [Elger, W., et al., *J. Ster. Biochem. Molec. Biol.* 55 (1995) 395–403] which is undesirable in this indication.

Nonsteroidal sulfatase inhibitors with a comparatively high sulfatase-inhibiting activity corresponding to estrone sulfamate have been reported on recently (Li P.-K. et al., *J. Ster. Biochem. Molec. Biol.* 59 (1996) 41–48).

Complete suppression of estrogenic activity was not previously observed in the nonsteroidal and steroidal sulfatase inhibitors with constant or improved sulfatase-inhibiting activity.

OBJECT AND SUMMARY OF THE INVENTION

Therefore, there is a need for compounds which limit or prevent the availability of estrogens in hormone-dependent tumors, wherein there is an interest in sulfatase inhibitors having no estrogenic active component.

Further, it is known that the estrogenicity of estradiol can be varied through specific substitution in the D ring. Oral effectiveness can be decisively improved by substitution (alkylation or acetylation) of the proton residing geminal to the 17-hydroxy group. Substitution of the proton vicinal to the 17β-hydroxy group in the 16-position leads to reduced oral effectiveness. Substituting halogen or pseudohalogen leads to so-called braked, i.e., slightly or moderately effective, estrogens.

Further, since liver toxicity has been determined in long-term testing with 17-alkylated or acetylated estradiol derivatives, there is interest in highly effective estrogens with low toxicity in order to detach these compounds.

The object is met by providing new steroid sulfamoyloxy derivatives which are produced by suitable sulfamoylation reactions. It has been found that certain steroidal sulfamoyloxy compounds with more than one sulfamate grouping in the molecule, in particular those that are sulfamoylated at the characteristic positions for estrogenic activity, including substituents or side-chains (e.g., in the 7-position and/or 11-position) which can be found at the periphery of the steroid skeleton, show a clear increase in sulfatase activity with reduced estrogenic activity. In some cases, the estrogenicity can be reduced to such an extent that even antiestrogenic effects are observable.

According to the invention, it was found that compounds of the estradiol disulfamate and 16-halogen-estradiol disulfamate type have a greater sulfatase inhibition than any known compounds and, moreover, do not exhibit any estrogenicity. Due to the halogen substitution in the 16-position, the sulfatase-inhibiting activity is further increased compared with the unsubstituted compound.

Some monosulfamates, with the exception of the A-ring sulfamoyloxy compounds, show significant sulfatase activity with reduced estrogenicity. Synergistic effects are observed in the presence of two or more such pharmacophores in a molecule. In some cases, these effects lead to a multiplying of the activity in comparison to the standard compounds, which was confirmed with respect to disulfamates and trisulfamates.

Due to the influencing of the estrogen biosynthesis, the direct sulfatase inhibition and other antiestrogenic effects, the availability of estrogens is limited or can be regulated, which can be utilized for the treatment of estrogen-dependent tumors and for diagnostics.

The direction of the pharmacological effect of the sulfamoyloxy compounds can be specifically changed depending on the substitution pattern, which makes it possible to use them as sulfatase inhibitors on the one hand and as estrogen components on the other hand. Surprisingly, in-vitro potential estrogen activities can be detected in some sulfamates by means of an estrogen transcription assay. In this test, 3,17-disulfamoyloxy compounds are found to be inactive.

The 16-substituted 3-monosulfamates which are the subject of this invention show an extraordinary therapeutic breadth. In addition to high sulfatase activity, these compounds are characterized by high estrogenicity. This is surprisingly high compared with the known highly effective estrone- or estradiol-3-sulfamates. According to the prior art, 16-halogen- or pseudohalogen-estradiols are less effective compared with estriol or estradiol. Estrogenicity is considerably increased by introducing the sulfamate group in the 3-position. Accordingly, 16α-bromoestradiol-3-sulfamate applied orally in vivo is five times more effective than estriol and three times more effective than estradiol-3-sulfamate. Based on these findings, new orally effective estrogens are available for contraception and hormone replacement therapy on the one hand and for diagnostics in the application of radioactive species (PET) on the other hand.

In marked form, especially in the case of short-lived isotopes such as [$^{18}$F], [$^{76}$Br] or Tc, etc., the compounds according to the invention represent potential markers for diagnosing diseased tissue, including cancerous tissue, due to their target specificity relative to steroid sulfatase as well as estrogen receptors.

The compounds according to the invention are extremely effective sulfatase inhibitors which are suitable, by themselves or in combination with other active components, e.g., aromatase inhibitors or antiestrogens, for the treatment of diseases in relation to inhibition of sulfatases or estrogens, e.g., for treating hormone-dependent tumors.

Further, some of the steroidal sulfamoyloxy compounds in combination with a gestagen are also important means for contraception and for the treatment of climacteric complaints.

The compounds according to the invention having the general formula I, can be used as pharmaceuticals. Production of these preparations is carried out by galenic methods, known per se, by mixing with organic and/or inorganic inert carrier materials suitable for enteral, percutaneous or parenteral applications.

Suitable dosages can be determined routinely by determining bioequivalence relative to a known sulfatase inhibitor or a known estrogen. The dosage of the compounds according to the invention ranges from 0.001 to 200 mg per day.

BRIEF DESCRIPTION OF THE INVENTION

The sulfamoyloxy compounds according to the invention are steroids of the gonane type and D-homo-gonane type according to formula I,

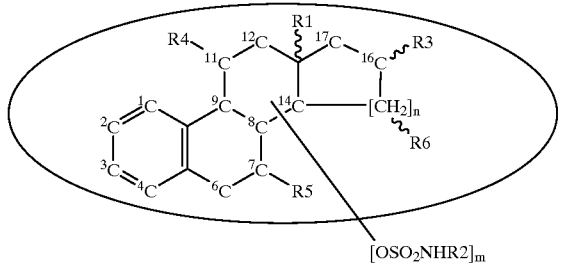

I wherein there is possibly an additional double bond between C atoms 9 and 11, 8 and 9, 8 and 14, 14 and 15, 15 and 16, 6 and 7, or 7 and 8, or wherein there are possibly two double bonds between C atoms 8, 9, 14, 15 or 8, 9, 7, 6, or which contain a cyclopropane grouping or epoxide grouping with α- or β-orientation between C atoms 14 and 15 or 15 and 16, wherein C atoms 2, 3, 4, 6, 7, 11, 12, 15, 16 and/or 17 are unsubstituted or are substituted by $C_1$–$C_6$-alkyloxy, $C_1$–$C_4$-alkyloxy-$C_1$–$C_4$-alkyloxy, hydroxy-$C_1$–$C_4$-alkyloxy, $C_1$–$C_6$-alkanoyloxy or tris-($C_1$–$C_4$-alkyl)-silyloxy or hydroxy, wherein a keto grouping —C(═O)—, which is possibly protected in the form of a ketal, thioketal, cyanhydrin, cyanosilyl ether or a geminal hydroxyethinyl group, can also be present instead of a secondary hydroxy group —CH(OH)—, wherein n=1 or 2, $R_1$=α-methyl or β-methyl or α-ethyl or β-ethyl for H, the sulfamoyloxy group —OSO$_2$NHR$_2$ preferably resides at C-1,-2,-3,-4,-6,-7,-11,-15, -16 and/or -17 and further also at groups $R_4$ and/or $R_5$, $R_2$=H, $C_1$–$C_5$-alkyl, $C_1$–$C_3$-alkyl with annelated saturated ring, aryl-$C_1$–$C_3$-alkyl, $C_1$–$C_5$-alkanoyl, $C_3$–$C_7$-cycloalkylcarbonyl, $R_3$=H, OH or halogen such as chlorine, bromine, [$^{76}$Br] bromine, iodine [$^{125}$I]- or [$^{131}$I]-iodine, astatine, fluorine or [$^{18}$F] fluorine, pseudohalogen such as $N_3$, CN, SCN or SeCN, or $C_1$–$C_3$-alkyl, $C_3$–$C_7$-cycloalkyl, 1',1'-cycloalkyl or aryl-$C_1$–$C_3$-alkyl, $R_4$=H, aryl or $C_1$–$C_{12}$-alkyl, $R_5$=H, $C_1$–$C_{12}$-alkyl or $C_1$–$C_{12}$-alkylaryl, $R_6$=H or halogen, such as chlorine, bromine, [$^{76}$Br] bromine, fluorine, [$^{18}$F] fluorine or astatine, and m=1 to 5, preferably 1 to 3, with the condition that $R_3$ is different than H and OH when m is 1 and the sulfamoyloxy group is bonded to the aromatic A ring, and salts thereof, particularly pharmaceutically acceptable salts.

In this connection, 1',1'-cycloalkyl stands for spiro-$C_3$–$C_6$-alkyl or -alkenyl, aryl-$C_1$–$C_3$-alkyl stands, e.g., for phenyl-$C_1$–$C_3$-alkyl such as benzyl or for heteroar-$C_1$–$C_3$-alkyl, wherein heteroaryl stands for the following groups, for example: pyridine, picoline, lutidine, collidine, quinoline, acridine, pyridazine, pyrimidine, pyrazine, triazine, pterine, pyrrole, indole, pyrazole, imidazole, 1,2,3-triazole, 1,2,4-triazole, tetrazole, oxazole, thiazole or thiodiazole. In addition to $C_3$–$C_7$-cycloalkyl, saturated annelated rings include hydrogenated heterocyclic rings such as piperidine, piperazine, pyrrolin, pyrolidine, oxazoline, oxazolidine, thiazoline, thiazolidine, imidazoline or imidazolidine. By aryl is meant a heteroaryl substituent in the aforementioned sense or an o-, m- or p-substituted phenyl group (substituents of a phenyl group are, e.g., halogen, $C_1$–$C_5$-alkylthio, $C_1$–$C_5$-alkyloxy, hydroxy, $C_1$–$C_5$-alkyl, hydroxy-$C_1$–$C_5$-alkyl, $C_1$–$C_5$-alkanoyl, CN, amino, mono- or di-$C_1$–$C_3$-alkylamino, nitro or CHO and acetals and oximes having the formula —CH(OR)(OR') and —CH═NOR thereof, wherein R and R' stand for H or $C_1$–$C_5$-alkyl or R and R' together stand for $C_2$–$C_4$-alkylene).

Preferably, $R_1$=α- or β-methyl or α-ethyl or β-ethyl, n=1 or 2, $R_3$=H, OH, chlorine, bromine, fluorine, $N_3$, CN, SCN or SeCN, m=1 to 3, $R_2$=in the sulfamoyloxy group or groups (—OSO$_2$NHR$_2$), H and/or $C_1$–$C_5$-alkyl, $C_1$–$C_5$-alkanoyl, or $C_3$–$C_7$-cycloalkylcarbonyl, $R_4$=H, aryl or $C_1$–$C_{12}$-alkyl, $R_5$=H, $C_1$–$C_{12}$-alkyl or $C_1$–$C_{12}$-alkylaryl, $R_6$=H, chlorine, bromine, or fluorine, wherein a sulfamoyloxy group can preferably be fixed to the aromatic A ring and/or to an aryl group $R_4$ and, further, to C atoms 7, 11, 15, 16, or 17, under the condition that $R_3$ is different than H and OH when m is 1 and the sulfamoyloxy group is bonded to the aromatic A ring, and salts thereof.

In further preferred compounds of formula I:

$R_1$=β-methyl or β-ethyl, $R_3$=bromine, [$^{76}$Br] bromine, fluorine, [$^{18}$F] fluorine, [$^{125}$I]- or [$^{131}$I]-iodine, or astatine $R_6$=bromine, [$^{76}$Br] bromine, fluorine, or [$^{18}$F] fluorine, m=1 to 2, and $R_2$, $R_4$, $R_5$ and n have the above-indicated meanings, wherein one of the sulfamoyloxy groupings is positioned at the aromatic A ring and when m=2 the second sulfamoyloxy group (—OSO$_2$NHR$_2$) is in the 17α- or 17β-position, and salts thereof.

Another preferred group of compounds according to the invention relates to those of formula 1, wherein there is possibly an additional double bond between C atoms 9 and 11, 8 and 9, 8 and 14, 14 and 15, 6 and 7, or 7 and 8, or wherein there are two double bonds between C atoms 8, 9, 14, 15 or 8, 9, 7, 6, or which contain a cyclopropane grouping or epoxide grouping with α-orientation or β-orientation between C atoms 14 and 15, wherein C atoms 2, 3, 4, 6, 7, 11, 12, 15, 16 and/or 17 are possibly substituted by $C_1$–$C_6$-alkyloxy, $C_1$–$C_4$-alkyloxy-$C_1$–$C_4$-alkyloxy, hydroxy-$C_1$–$C_4$-alkyloxy, $C_1$–$C_6$-alkanoyloxy or tris-($C_1$–$C_4$-alkyl)silyloxy, hydroxy, wherein a keto grouping which can be protected in the form of a ketal, thioketal, cyanhydrin, cyanosilylether or a geminal hydroxyethinyl group can also be present instead of a secondary hydroxy group, wherein n=1 or 2, $R_1$=α-methyl or β-methyl or β-ethyl for H, $R_3$=H or halogen such as chlorine, bromine, [$^{76}$Br] bromine, iodine, astatine, fluorine or [$^{18}$F] fluorine, the sulfamoyloxy group —$OSO_2NHR_2$ preferably resides at C-1,-2,-3-,-4,-6,-7,-11,-15,-16 and/or -17 and further also at groups $R_4$ and/or $R_5$, and $R_2$=H, $C_1$–$C_5$-alkyl, $C_1$–$C_3$-alkyl with annelated saturated ring or is aryl-$C_1$–$C_3$-alkyl, $R_4$=aryl or $C_1$–$C_{12}$-alkyl, $R_5$=$C_1$–$C_{12}$-alkyl, $R_6$=halogen, such as chlorine, bromine, [$^{76}$Br] bromine, [$^{18}$F] fluorine, fluorine or astatine, m=1 to 5, preferably 1 to 3, under the condition that $R_3$ is different than H when, where m=1, the sulfamoyloxy group is bonded to the aromatic A ring, and salts thereof.

The following compounds of the invention are particularly preferred:

3,17β-disulfamoyloxy-13β-methyl-1,3,5(10)-gonatriene, 3,17β-disulfamoyloxy-13β-methyl-D-homo-1,3,5(10)-gonatriene, 3,17β-disulfamoyloxy-13β-methyl-8α-D-homo-1,3,5(10)-gonatriene, 3,17β-disulfamoyloxy-13β-ethyl-1,3,5(10)-gonatriene, 3,17β-disulfamoyloxy-13β-methyl-1,3,5(10),7(8)-gonatetraene, 3,17β-disulfamoyloxy-13β-methyl-1,3,5(10)8,6-gonapentaene, 3,17β-disulfamoyloxy-13β-methyl-1,3,5(10),8-gonatetraene, 3,17β-disulfamoyloxy-13β-methyl-1,3,5(10),8,14-gonapentaene, 3,17β-disulfamoyloxy-13β-methyl-1,3,5(10),8(14)-gonatetraene, 3,17β-disulfamoyloxy-13β-methyl-1,3,5(10),9(11)-gonatetraene, 3,17β-disulfamoyloxy-13β-ethyl-1,3,5(10),9(11)-gonatetraene, 3,17β-disulfamoyloxy-14β,15β-methylene-13β-methyl-1,3,5(10)8-gonatetraene, 3,17α-disulfamoyloxy-14β,15β-methylene-13β-methyl-1,3,5(10)8-gonatetraene, 3,17β-disulfamoyloxy-14α,15α-methylene-13β-methyl-1,3,5(10)8-gonatetraene, 3,17α-disulfamoyloxy-14α,15α-methylene-13β-methyl-1,3,5(10)8-gonatetraene, 16α-bromo-3,17β-disulfamoyloxy-13β-methyl-1,3,5(10)-gonatriene, 16α-bromo-3,17β-disulfamoyloxy-13β-ethyl-1,3,5(10)-gonatriene, 16β-bromo-3,17β-disulfamoyloxy-13β-methyl-1,3,5(10)-gonatriene, 16α-chloro-3,17β-disulfamoyloxy-13β-methyl-1,3,5(10)-gonatriene, 16α-chloro-3,17β-disulfamoyloxy-13β-ethyl-1,3,5(10)-gonatriene, 16β-chloro-3,17β-disulfamoyloxy-13β-methyl-1,3,5(10)-gonatriene, 3,17β-disulfamoyloxy-16α-fluoro-13β-methyl-1,3,5(10)-gonatriene, 3,17β-disulfamoyloxy-16α-fluoro-13β-ethyl-1,3,5(10)-gonatriene, 16α-bromo-3-sulfamoyloxy-13β-methyl-1,3,5(10)-gonatrien-17β-ol, 16α-fluoro-3-sulfamoyloxy-13β-methyl-1,3,5(10)-gonatrien-17β-ol, 16α-chloro-3-sulfamoyloxy-13β-methyl-1,3,5(10)-gonatrien-17β-ol, 17β-sulfamoyloxy-13β-methyl-1,3,5(10)-gonatrien-3-ol, 17β,16β-dihydroxy-3-sulfamoyloxy-13β-methyl-1,3,5(10)-gonatriene-16,17-sulfate, 3-sulfamoyloxy-16,17-(2',2'-propylenedioxy)-13β-methyl-1,3,5(10)-gonatriene, 3,16α,17β-trisulfamoyloxy-13β-methyl-1,3,5(10)-gonatriene, 16α-bromo-3-sulfamoyloxy-13β-methyl-1,3,5(10)-gonatrien-17β-on, 16α-bromo-3-sulfamoyloxy-13β-ethyl-1,3,5(10)-gonatrien-17β-on, 3,17α-disulfamoyloxy-13β-methyl-1,3,5(10)-gonatriene, 17α-sulfamoyloxy-13β-methyl-1,3,5(10)-gonatrien-3-ol, 16α-fluoro-17β-sulfamoyloxy-13β-methyl-1,3,5(10)-gonatrien-3-ol, 16α-bromo-17β-sulfamoyloxy-13β-methyl-1,3,5(10)-gonatrien-3-ol, 17β-sulfamoyloxy-13β-ethyl-1,3,5(10)-gonatrien-3-ol, 3-methoxy-17β-sulfamoyloxy-13β-methyl-1,3,5(10)-gonatriene, 3-methoxy-17β-sulfamoyloxy-13β-ethyl-1,3,5(10)-gonatriene.

The compounds according to the invention are produced, for example, in that, in a manner known per se, steroid alcohols having the following general formula II,

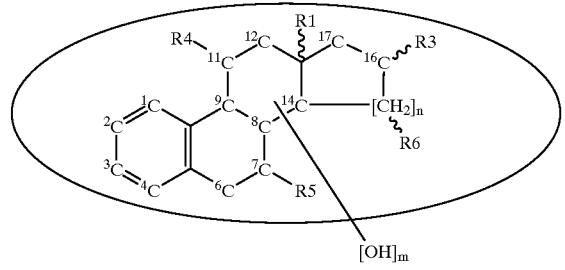

II where the substituents have the aforementioned meanings, are dissolved or suspended in a suitable solvent, are partially or quantitatively converted to alcoholates with a base, which is also possibly carried out by phase transfer catalysis, or are combined with auffer in the form of a tertiary amine, a pyridine base or an anhydrous salt, and are reacted with amidosulfuric acid chlorides to form the corresponding amidosulfonates optionally, where m=1 to 5, wherein the amidosulfuric acid chlorides can be N-alkylated or N-alkanoylated.

Halogenated carbohydrates such as methylene chloride or chloroform, ethyl acetate, tetrahydrofuran, methyl tert-butyl ether or ether, acetonitrile, DMF, DMSO, benzene, toluene or mixtures thereof are preferably used as solvents.

NaH, CaH$_2$, lithium alkyls, LDA, lithium naphthalide, potassium tert-butylate, KOH or NaOH, possibly combined with a phase transfer salt, are preferably used as bases for conversion into alcoholates.

Triethylamine, 2,6- or 2,4,6-alkylated pyridine bases, anhydrous K$_2$CO$_3$ or Na$_2$CO$_3$, the latter combined, as the case may be, with a phase transfer salt or a crown ether, are preferably used as buffers.

Sulfamoylation is carried out in stages with amidosulfuric acid chlorides such as sulfamoyl chloride, N-alkyl- or N-alkanoyl-amidosulfuric acid chlorides, possibly of different types.

Care is taken during the reaction for optimum mixing, possibly accompanied by cooling, wherein ultrasonic is advantageously applied.

EXAMPLES OF THE INVENTION

The following examples serve to describe the invention more fully without limiting the invention in any way.

EXAMPLE 1

16β,17β-Dihydroxy-3-sulfamoyloxy-13β-methyl-1,3,5 (10)-gonatriene-16,17-sulfate.

147 mg (0.373 mMole) of 16β,17β-dihydroxy-3-methoxymethyloxy-1,3,5(10)-gonatriene-16,17-sulfate are dissolved in 5 ml of acetonitrile and 45 μl HCL (1M) are added. The reaction mixture is heated for 10 minutes at 110° C. accompanied by stirring, the solvent is distilled off, and 6 ml of methylene chloride (distilled over P$_2$O$_5$), 700 mg of anhydrous Na$_2$CO$_3$, and 180 mg (1.56 mMole) of sulfamoyloxy chloride are added at room temperature. The reaction mixture is vigorously stirred. After the reaction has been completed (approximately 6 hours), water is added and extraction is carried out with ether. After the evaporation of the solvent, the residue is absorbed with a small amount of acetonitrile and chromatographed on an HPLC column (ET 125/8/4 Nucleosil 120-5C18 Macherey-Nagel). Detection is carried out with an L-4500 DAD at a wavelength of 275 nm. Elution is carried out with acetonitrile and the substance which is eluted at an R$_f$ of 7.3 minutes is concentrated in a vacuum. 34.7 mg (60%) of a powdery product is isolated and was crystallized from acetonitrile.

F$_{MeCN}$: 195 to 198° C.; Elementary analysis: calculated: C: 50.4; H: 5.4; N: 3.3; S: 14.9; actual: C: 49.3; H: 6.1; N: 3.5; S: 14.2; MS: c/m 429.0934 (M$^+$), 350.1180 (55%, M$^+$—HNSO$_2$), (50%, M$^+$ —HNSO$_2$,—SO$_3$); UV$_{Max}$[nm]: 270 (acetonitrile); IR [cm$^{-1}$; KBr]: 3504, 3404, 3308, 1489, 1447, 1382, 1202, 991, 839, 702, 641, 540 $^{13}$C-NMR(ppm; CDCl$_3$): C(1) 127.1, C(2) 120.0, C(3) 149.3, C(4) 122.7, C(5) 138.7, C(10) 138.4, C(12) 37.4, C(13) 44.1, C(14) 47.9, C(15) 31.3, C(16) 82.8, C(17) 91.3, C(18) 13.0.

EXAMPLE 2

3-Sulfamoyloxy-16,17-(2',2'-propylenedioxy)-13β-methyl-1,3,5(10)-gonatriene.

75 mg (0.23 mM) of 16,17-(2',2'-propylenedioxy)-13β-methyl-1,3,5(10)-gonatrien-3β-ol are dissolved in 5 ml of methylene chloride. After adding 500 mg of anhydrous Na$_2$CO$_3$ and 30 mg (0.26 mM) of H$_2$NSO$_2$Cl, the solution is vigorously stirred at room temperature for 60 hours. During this time, additional portions of the reagent (8*10 mg) are added. The suspension is worked up by stirring in water and the steroid is extracted with ether. After the organic phase has been washed to neutral in water, drying is carried out with sodium sulfate and the solvent is evaporated in a vacuum. The remaining residue is dissolved in a small amount of acetonitrile and separated by preparative HPLC (ET 125/8/4 Nucleosil 120-5C18 Macherey-Nagel) using acetonitrile as eluent (detection: L 4500 DAD, 275 nm, R$_f$ 0 8.7 minutes), wherein 26.3 mg (24.75%) in the form of a white powder was isolated after recrystallization from acetonitrile.

F.: 180 to 185° C.; Elementary analysis: calculated: C(61.9), H(7.1), N(3.4), S(7.9), actual: C(62.1), H(6.9), N(3.6), S(7.9), MS: (c/m): 407.2 (M$^+$) calculated for C$_{21}$H$_{29}$NO$_5$S; UV$_{Max}$[nm]: 275 (acetonitrile); IR [cm$^{-1}$; KBr]: 3464, 3385, 1604, 1497, 1444, 1371, 1281, 1250, 1205, 1152, 1059, 863.

EXAMPLE 3

3,17β-Disulfamoyloxy-13β-methyl-1,3,5(10)-gonatriene.

70 mg (0.26 mM) of 13β-methyl-1,3,5(10)-gonatriene-3, 17β-diol, 500 mg of K$_2$CO$_3$, and 30 mg of Bu$_4$NBr are suspended in 3 ml of methylene chloride and 1 ml of ethyl acetate and, after the addition of 90 mg (0.68 mM) of H$_2$NSO$_2$Cl, the suspension is treated in an ultrasonic bath with the exclusion of water at 25 to 35° C. After approximately 60 minutes, an additional 45 mg (0.34 mM) of H$_2$NSO$_2$Cl are added and stirring is carried out in water for 2 hours. After extraction of the steroid with ether, the solvent is evaporated in a vacuum and the residue is chromatographed on silica gel 60. Elution with toluene/acetone (10:1) yields 21 mg (19%) of the disulfamate which can be crystallized from ethyl acetate/n-hexane.

F.: 191 to 194° C.; UV$_{Max}$[nm]: 275 (acetonitrile); IR [cm$^{-1}$; KBr]: 3266, 3302, 3338, 3390 (NH), 1540, 1368, 1322, 1184, 930, 871, 817; MS c/m: 333, 1370 (M$^+$ —H$_2$NSO$_3$H, calculated for C$_{18}$H$_{23}$O$_3$NS; ES$^+$: 452.9 (M+Na); 469.0 (M+K) calculated for C$_{18}$H$_{26}$N$_2$O$_6$S$_2$.

EXAMPLE 4

17β-Sulfamoyloxy-13β-methyl-1,3,5(10)-gonatrien-3-ol.

70 mg (0.26 mM) of 13β-methyl-1,3,5(10)-gonatrien-3, 17β-diol and 500 mg of Na$_2$CO$_3$ are suspended in 5 ml of methylene chloride and, after adding 100 mg (0.86 mM) of H$_2$NSO$_2$Cl and another 100 mg (0.86 mM) after 6 hours, the suspension is treated in an ultrasonic bath with the exclusion of water for 16 hours. The suspension is worked up by stirring in water and the steroid is extracted with ether. After evaporation of the solvent, the remaining residue is chromatographed on silica gel 60. A toluene/acetone mixture (7:1) is used as eluent. 25 mg (27.7%) of the 17-sulfamate are isolated and can be crystallized from toluene/acetone or ethyl acetate/n-hexane.

F.: 165 to 170° C.; Elementary analysis: calculated: C: 59.0 H: 6.6 N: 4.0 S: 8.6; actual: C: 61.5 H: 7.1; N: 4.0 S: 9.1; MS: c/m: actual 351.1539 (M$^+$), calculated: 351.1540 for C$_{18}$H$_{25}$NO$_4$S; UV$_{Max}$[nm]: 284 (acetonitrile); IR [cm$^{-1}$; KBr]: 3414, 3278 (NH), 1346, 1177, 964, 869, 586.

EXAMPLE 5

3-Methoxy-17β-sulfamoyloxy-13β-methyl-1,3,5(10)-gonatriene.

500 mg (1.74 mM) of 3-methoxy-13β-methyl-1,3,5(10)-gonatrien-17β-ol, 500 mg of K$_2$CO$_3$, and 40 mg of Bu$_4$NBr are suspended in 10 ml of methylene chloride and, after the addition of 360 mg (3.1 mM) of H$_2$NSO$_2$Cl, are stirred intensively at room temperature until all of the starter material is consumed. After the reaction has been completed, the product is stirred into water and the steroid is extracted with ether. After the evaporation of the solvent, the remaining residue is crystallized from ethyl acetate/n-hexane or methylene chloride/n-hexane, resulting in 420 mg (66.3%) of 17-sulfamate.

$F_{Methyenechloride/n-hexane}$: 159 to 164° C.; $UV_{Max}$[nm]: 285 (acetonitrile); IR [cm$^{-1}$; CHCl$_3$]: 3445, 3344, 1603, 1567, 1546, 1496, 1376, 1252, 1245, 1181, 987, 972, 911; $R_t$ (Lichrosorb 100 C18, No. 1621225): 7.09.

EXAMPLE 6

3-Methoxy-17β-sulfamoyloxy-13β-ethyl-1,3,5(10)-gonatriene.

100 mg (0.33 mM) of 3-methoxy-13β-ethyl-1,3,5(10)-gonatrien-17β-ol, 500 mg of K$_2$CO$_3$, and 40 mg of Bu$_4$NBr are suspended in 3 ml of methylene chloride and 1 ml of ethyl acetate and, after the addition of 190 mg (1.64 mM) of H$_2$NSO$_2$Cl, are stirred intensively at room temperature until all of the starter material is consumed. After the reaction has been completed, the product is stirred into water and the steroid is extracted with ether. After the evaporation of the solvent, the remaining residue is chromatographed on silica gel 60. A methylene chloride/ethyl acetate mixture (20:1) serves as eluent. 90 mg (71.4%) of 17-sulfamate is obtained and can be recrystallized from methylene chloride/n-hexane.

F.: 178 to 184° C.; $UV_{Max}$[nm]: 283 (acetonitrile); IR [cm$^{-1}$; CHCl$_3$]: 3445, 3348, 1604, 1567, 1496, 1372, 1306, 1251, 989, 963, 915; MS ES$^-$: 364.5 (M–H) calculated for $C_{19}H_{27}NO_4S$ 365.48.

EXAMPLE 7

16α-Bromo-3,17β-disulfamoyloxy-13β-methyl-1,3,5(10)-gonatriene.

16α-Bromo-3-sulfamoyloxy-13β-methyl-1,3,5(10)-gonatrien-17β-ol.

70 mg (0.2 mM) of 16α-bromo-13β-methyl-1,3,5(10)-gonatrien-3,17β-diol, 500 mg of K$_2$CO$_3$ and 40 mg of Bu$_4$NBr are suspended in 3 ml of methylene chloride and 1 ml of ethyl acetate and, after the addition of 170 mg (1.47 mM) of H$_2$NSO$_2$Cl, are treated in an ultrasonic bath for 4 hours. The suspension is worked up by stirring in water and the steroid is extracted with ether. After evaporation of the solvent, the residue is chromatographed on silica gel 60. A methylene chloride/ethyl acetate mixture (20:1) serves as eluent. 10 mg of the polar fractions (60 mg) which appear uniform in a thin film are concentrated and separated by preparative HPLC (column RP 18, 2 ml/min, Jasco) using acetonitrile as eluent. 2 mg of 3,17-disulfamate ($R_t$ 5.9) and 3.5 mg of 3-monosulfamate ($R_t$ 6.36) are obtained.

$F_{Disulfamate/methylenechloride}$: 190 to 194° C.; MS-ES$^-$: 506.9 (509.1, isotope 81) (M–H) calculated exact mass 508.03 for $C_{18}H_{25}BrN_2O_6S_2$; $UV_{Max}$[nm]: 270 (acetonitrile); IR [cm$^{-1}$; KBr]: 3345, 3348 (NH), 1396, 1193, 917; $R_t$: 5.9 (RP 18, 2 ml/min); $^1$H-NMR [ppm; CD$_3$OD]: 7.32 d (1H), 7.05 qu (2H), 7.008 d (4H), 4.74 d (17α-H), 4.36 o (16β-H), 0.88 s (13-CH$_3$); $F_{3-Monosulfamate/methylenechloride/n-hexane}$: 94 to 104° C.; MS-ES$^-$: 428.3 (430.2, isotope 81) (M–H) calculated exact mass 429.0609 for $C_{18}H_{24}BrNO_4S$; $UV_{Max}$[nm]: 270 (acetonitrile); IR [cm$^{-1}$; CHCl$_3$]: 3608 (OH), 3452, 3348 (NH), 1395, 1185 (SO$_3$), 911 (NS); $R_t$ 6.36 (RP 18, 2 ml/min); $^1$H-NMR [ppm; CD$_3$OD]: 7.31 d (1H), 7.03 qu (2H), 7.01 d (4H), 4.13 o (16β-H), 3.88; d (17α-H), 0.776 s (13-CH$_3$).

EXAMPLE 8

16α-Bromo-17β-sulfamoyloxy-13β-methyl-1,3,5(10)-gonatrien-3-ol.

70 mg (0.2 mM) of 16α-bromo-13β-methyl-1,3,5(10)-gonatrien-3,17β-diol, 500 mg of K$_2$CO$_3$ and 40 mg of Bu$_4$NBr are suspended in 3 ml of methylene chloride and 1 ml of ethyl acetate and, after the addition of 90 mg (0.78 mM) of H$_2$NSO$_2$Cl, are treated in an ultrasonic bath for 2 hours. The suspension is worked up by stirring in water and the steroid is extracted with ether. After the evaporation of the solvent, the residue is chromatographed on silica gel 60. A methylene chloride/ethyl acetate mixture (20:1) serves as eluent. The middle fractions [$R_t$–0.635 (CH$_2$Cl$_2$ ethyl acetate 3:1)] are unified, concentrated and separated by preparative HPLC (column RP 18, 2 ml/min, Jasco) using acetonitrile as eluent. The fraction contains 2 main components $R_t$=8.219; $R_t$=9.83 RP18 prep. column or $R_t$=6.306 and 7.273 anal. column Spherisorb 100 C18 No. 1621225). The fraction with the more polar component ($R_t$=8.219) is separated and crystallized from methylene chloride/n-hexane.

$F_{Methylenechloride/n-hexane}$: 217 to 220° C.; $UV_{Max}$[nm]: 285; MS-E$^-$: 428.4 (430.4, isotope 81; M–H) calculated mass 429.06 for $C_{18}H_{24}BrNO_4$.

EXAMPLE 9

3,16α,17β-Trisulfamoyloxy-13β-methyl-1,3,5(10)-gonatriene.

100 mg (0.347 mM) of 13β-methyl-1,3,5(10)-gonatrien-3,16α,17β-triole, 500 mg of K$_2$CO$_3$ and 50 mg of BU$_4$NBr are suspended in 3 ml of methylene chloride and 1 ml of ethyl acetate and after the addition of 350 mg (3.02 mM) of H$_2$NSO$_2$Cl are treated in an ultrasonic bath for 5 hours. The suspension is worked up by stirring in water and the steroid is extracted with ether. After the evaporation of the solvent, the remaining residue is chromatographed on silica gel 60. A toluene/acetone mixture (7:1) serves as eluent. The polar fractions ($R_t$–0.09 gel, CH$_2$Cl$_2$/ethyl acetate 3:1) are concentrated and crystallized by means of methylene chloride.

F.: 115 to 122° C.; MS-ES$^-$: 524.4 (M–H) calculated mass 525.0909 for $C_{18}H_{27}N_3O_9S_3$; $UV_{Max}$[nm]: 270 (acetonitrile); IR [cm$^{-1}$; KBr]: 3388, 3284, 1549, 1486, 1369, 1180, 1000.8, 939, 921, 554; $R_t$: 7.29 (RP 18, 2 ml/min) or $R_t$: 5.717 (Spherisorb 100 C18, 0.5 ml/min); $^1$H-NMR [ppm; CD$_3$OD]: 7.32 d (1H), 7.05 qu (2H), 7.01 d (4H), 5.01 o (16β-H), 4.56 d (17α-H), 0.92 (13-CH$_3$).

EXAMPLE 10

16α-Fluoro-17β-sulfamoyloxy-13β-methyl-1,3,5(10)-gonatrien-3-ol.

70 mg (0.24 mM) of 16α-fluoro-13β-methyl-1,3,5(10)-gonatrien-3,17β-ol and 500 mg of K$_2$CO$_3$ are suspended in 3 ml of methylene chloride and 1 ml of ethyl acetate and after the addition of 100 mg (0.87 mM) of H$_2$NSO$_2$Cl are treated in an ultrasonic bath at room temperature for 8 hours. The suspension is then stirred in water and the steroid is extracted with ether. After the evaporation of the solvent, the remaining residue is chromatographed on silica gel 60. A methylene chloride/ethyl acetate mixture (20:1) serves as eluent. 21 mg (23.6%) of the 17-sulfamate are obtained and can be recrystallized from methylene chloride/n-hexane.

F.: 230 to 236° C.; MS-ES$^-$: 368.5 (M–H) calculated mass 369.45 for $C_{18}H_{24}NO_4S$; $UV_{Max}$[nm]: 282 (acetonitrile); IR [cm$^{-1}$; KBr]: 3268, 3375, 3552, 1607, 1578, 1552, 1493, 1440, 1362, 1179, 1000, 929, 850; $R_t$: 7.99 (RP18, 2 ml/min) or $R_t$: 6.149 (Spherisorb 100 C18, 0.5 ml/min acetonitrile).

EXAMPLE 11

3,17α-Disulfamoyloxy-13β-methyl-1,3,5(10)-gonatriene.

3-Sulfamoyloxy-13β-methyl-1,3,5(10)-gonatrien-17α-ol.

52 mg (0.19 mM) of 13β-methyl-1,3,5(10)-gonatrien-3,17α-diol are dissolved 10 ml acetonitrile accompanied by heat and 500 mg of (anhydrous) $Na_2CO_3$ are added. After the solution is cooled, 30 mg (0.26 mM) of $H_2NSO_2Cl$ are added and the solution is stirred vigorously. At one-hour intervals, 9 portions of $H_2NSO_2Cl$ are added for every 10 mg. After 9 hours, the solution is worked up by stirring in diluted hydrochloric acid solution and the steroid is extracted with ether. The residue remaining after the concentration of the extract is absorbed in 4 ml of an acetonitrile/ethanol mixture (3:1) and separated by preparative HPLC (ET 125/8/4 Nucleosil 120-5C18 Macherey-Nagel, RT7.0) using acetonitrile as eluent. After concentration of the fraction with the $R_t$=7.0 ($R_f$=0.2; gel benzene; acetone=4:1) or $R_t$=8.1 ($R_f$=0.22 gel, benzene/acetone 4:1), 28.9 mg of the 3,17α-disulfamate (35.4%) and 9.8 mg (14.6%) of the 3 monosulfamate are isolated in the form of white powder.

$F._{Disulfamate}$: 170 to 172° C.; MS-ES$^-$: 429.4 (M–H) calculated mass 430.53 for $C_{18}H_{26}N_2O_6S_2$; ES$^+$: 883 (2M+Na); $UV_{Max}$[nm]: 270 (acetonitrile); IR [cm$^{-1}$; KBr]: 3396, 3336, 3264, 1601, 1547, 1489, 1372, 1327, 1184, 930; $F._{3-Monosulfamate}$: 180 to 189° C.; MS c/m: 351.2 (M$^+$) calculated 351.15 for $C_{18}H_{25}NO_4S$; 333.2 (M$^+$—H$_2$O), calculated for $C_{18}H_{23}O_3NS$; $UV_{Max}$[nm]: 269 (acetonitrile); IR [cm$^{-1}$; KBr]: 3550, 3370, 3235, 3185, 1602, 1571, 1490, 1381, 1274, 1211, 1179, 1145, 923, 813, 720, 619, 556, 543.

EXAMPLE 12

17α-Sulfamoyloxy-13β-methyl-1,3,5(10)-gonatrien-3-ol.

136 mg (0.5 mM) of 13β-methyl-1,3,5(10)-gonatrien-3,17α-diol are dissolved in 14 ml acetonitrile accompanied by heat and 500 mg of (anhydrous) $Na_2CO_3$ are added. After the solution is cooled, 100 mg (0.86 mM) of $H_2NSO_2Cl$ are added and the solution is stirred vigorously. For purposes of working up, the solution is stirred in diluted hydrochloric acid solution for 90 min and the steroid is extracted with ether. The residue remaining after the concentration of the extracts is absorbed in 4 ml of an acetonitrile/ethanol mixture (3:1) and separated by preparative HPLC (ET 125/8/4 Nucleosil 120-5C18 Macherey-Nagel, RT7.0) using acetonitrile/water (19: [HK1]1) as eluent. After concentration of the fraction with the $R_t$=7.55 ($R_f$=0.55; gel, benzene/acetone=4:1), 21.9 mg (12.5%) of the 17α-sulfamate are isolated in the form of a white powder.

F.: 114 to 120° C.; MS: c/m: 294.2 (M$^+$-97 (HO$_3$SNH$_2$) calculated for $C_{18}H_{22}O$ corresponds to $C_{18}H_{25}NO_4S$ (351.15); ES$^-$: 350.4 (M–H); $UV_{Max}$[nm]: 283 (acetonitrile); IR [cm$^{-1}$; KBr]: 3370, 3150, 1606, 1583, 1495, 1446, 1298, 1236, 1065, 685, 545.

EXAMPLE 13

3,17β-Disulfamoyloxy-13β-ethyl-1,3,5(10)-gonatriene.

100 mg (0.35 mM) of 130-ethyl-1,3,5(10)-gonatrien-3,17β-diol, 500 mg of $K_2CO_3$ and 40 mg of $Bu_4NBr$ are suspended in 2 ml of methylene chloride and 2 ml of ethyl acetate and after the addition of 260 mg (2.25 mM) of $H_2NSO_2Cl$ are treated in an ultrasonic bath for 2.5 hours. For working up, the suspension is then stirred in water and the steroid is extracted with ether. After the evaporation of the solvent, the remaining residue is chromatographed on silica gel 60. A toluene/acetone mixture (10:1) serves as eluent. 31 mg (20%) of the disulfamate are isolated from the polar fractions and can be recrystallized from methylene chloride/n-hexane.

F.: 173 to 178° C.; MS-ES$^+$: 467.0 (M+Na), 911.9 (2M+Na); ES$^-$: 443.5 (M–H), 887 (2M–H); $UV_{Max}$[nm]: 270 (acetonitrile); IR [cm$^{-1}$; KBr]: 3392, 3280, 1603, 1549, 1488, 1363, 1184, 1179, 1138, 921, 551; $R_t$: 5.955 (Lichrosorb 100 C18, 0.5 ml/min) or $R_t$: 7.67 (RP18, 2 ml/min); $^1$H-NMR [ppm CD$_3$OD]: 7.31 d (1H), 7.04 qu (2H), 7.01 d (4H), 4.64 qu (17α-H), 1.00 t (13-ethyl).

EXAMPLE 14

17β-Sulfamoyloxy-13β-ethyl-1,3,5(10)-gonatrien-3-ol.

50 mg (0.17 mM) of 13β-ethyl-1,3,5(10)-gonatrien-3, 17β-diol and 500 mg of $K_2CO_3$ and 40 mg of $Bu_4NBr$ are suspended in 2 ml of methylene chloride and 2 ml of ethyl acetate and after the addition of 115 mg (1 mM) of $H_2NSO_2Cl$ are treated in an ultrasonic bath for 6 hours. For working up, the suspension is then stirred in water and the steroid is extracted with ether. After the evaporation of the solvent, the remaining residue is chromatographed on silica gel 60. A toluene/acetone mixture (10:1) serves as eluent. The fractions with $R_f$=0.41 (gel, toluene/acetone 4:1) or $R_f$=0.62 (gel, CH$_2$Cl$_2$/ethyl acetone 3:1), $R_t$=8.506 (RP 18) are concentrated (15 mg=23.8%) and crystallized from methylene chloride/n-hexane.

F.: 174 to 176° C.; MS-ES$^-$: 364.5 (M–H), 729.5 (2M–H); $UV_{Max}$[nm]: 285 (acetonitrile); IR [cm$^{-1}$; CHCl$_3$]: 3592, 3445, 3348, 1608, 1545, 1497, 1443, 1374, 1184, 1065, 917; $R_t$: 8.506 (RP18, 2 ml/min).

EXAMPLE 15

3,17β-Disulfamoyloxy-16α-fluoro-13β-methyl-1,3,5(10)-gonatriene.

15 mg of 16α-fluoro-13β-methyl-1,3,5(10)-estratrien-3,17β-diol are dissolved in 1 ml of DMF and 45 mg of $H_2NSO_2Cl$ are added accompanied by cooling under inert gas and stirring. After two hours, the solution is stirred into a saturated bicarbonate solution for working up and the steroid is extracted with methylene chloride. The residue remaining after concentration of the methylene chloride extract is chromatographed on silica. After eluting with methylene chloride/ethyl acetate (6:1), the fractions with $R_F$=0.6 [(silica gel; methylene chloride/ethyl acetone 3:1) ($R_t$=5.833; RP 18, acetonitrile)] are concentrated and crystallized from methylene chloride.

F.: 178 to 184° C.; MS-ES$^-$: 447.4 (M–H), 894.7 (2M–H), 671 (3M$^-$–H); Ms-ES$^+$: 471.2 (M+Na), 919.2 (2M+Na), 695.6 (3M+2Na); $R_t$: 5.833 (RP 18; 0.5 ml/min CH$_3$CN).

EXAMPLE 16

The following can be produced analogously (corresponding to Examples 1–15):

3,17β-disulfamoyloxy-13β-methyl-D-homo-1,3,5(10)-gonatriene, 3,17β-disulfamoyloxy-13β-methyl-8α-D-homo-1,3,5(10)-gonatriene, 3,17β-disulfamoyloxy-13β-methyl-1,3,5(10),7(8)-gonatetraene, 3,17β-disulfamoyloxy-13β-methyl-1,3,5(10)8,6-gonapentaene, 3,17β-disulfamoyloxy-13β-methyl-1,3,5(10),8-gonatetraene, 3,17β-disulfamoyloxy-13β-methyl-1,3,5(10),8,14-gonapentaene, 3,17β-disulfamoyloxy-13β-methyl-1,3,5(10),8(14)-gonatetraene, 3,17β-disulfamoyloxy-13β-methyl-1,3,5(10),9(11)-gonatetraene, 3,17β-disulfamoyloxy-13β-ethyl-1,3,5(10),9(11)-gonatetraene, 3,17β-disulfamoyloxy-14β,15β-methylene-13β-methyl-1,3,5(10)8-gonatetraene, 3,17α-disulfamoyloxy-14β,15β-methylene-13β-methyl-1,3,5(10)8-gonatetraene, 3,17β-disulfamoyloxy-14α,15α-methylene-13β-methyl-1,3,5(10)8-gonatetraene, 3,17α-disulfamoyloxy-14α,15α-methylene-13β-methyl-1,3,5(10)8-gonatetraene, 16α-bromo-3,17β-disulfamoyloxy-13β-ethyl-1,3,5(10)-gonatriene, 16β-bromo-3,17β-disulfamoyloxy-13β-methyl-1,3,5(10)-gonatriene, 16α-chloro-3,17β-disulfamoyloxy-13β-methyl-1,3,5(10)-gonatriene, 16α-chloro-3,17β-disulfamoyloxy-13β-ethyl-1,3,5(10)-gonatriene, 16β-chloro-3,17β-disulfamoyloxy-13β-methyl-1,3,5(10)-gonatriene, 16α-chloro-3-sulfamoyloxy-13β-methyl-1,3,5(10)-gonatrien-17β-ol, 16α-bromo-3-sulfamoyloxy-13β-methyl-1,3,5(10)-gonatrien-17β-on, 16α-bromo-3-sulfamoyloxy-13β-ethyl-1,3,5(10)-gonatrien-17β-on, 3,17α-disulfamoyloxy-13β-methyl-1,3,5(10)-gonatriene, 17α-sulfamoyloxy-13β-methyl-1,3,5(10)-gonatrien-3-ol, 16α-fluoro-17β-sulfamoyloxy-13β-methyl-1,3,5(10)-gonatrien-3-ol, 16α-bromo-17β-sulfamoyloxy-13β-methyl-1,3,5(10)-gonatrien-3-ol, 17β-sulfamoyloxy-13β-ethyl-1,3,5(10)-gonatrien-3-ol, 3-methoxy-17β-sulfamoyloxy-13β-methyl-1,3,5(10)-gonatriene, 3-methoxy-17β-sulfamoyloxy-13β-ethyl-1,3,5(10)-gonatriene.

While the foregoing description and examples represent the present invention, it will be obvious to those skilled in the art that various changes may be made therein without departing from the true spirit and scope of the present invention.

What is claimed is:

1. Steroids of the gonane type and D-homo-gonane type and salts thereof, having the general formula I:

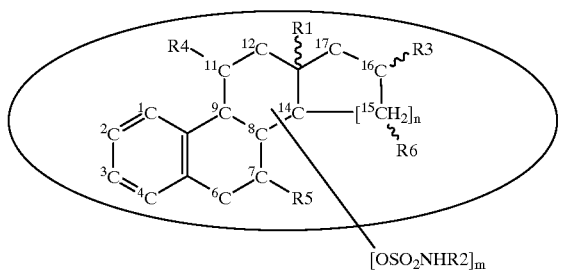

I wherein

C atoms 2, 3, 4, 6, 7, 11, 12, 15, 16 and 17 are each independently unsubstituted or substituted by $C_1$–$C_6$-alkyloxy, $C_1$–$C_4$-alkyloxy-$C_1$–$C_4$-alkyloxy, hydroxy-$C_1$–$C_4$-alkyloxy, $C_1$–$C_6$-alkanoyloxy, tris-($C_1$–$C_6$-alkyl)-silyloxy or hydroxy, wherein each secondary hydroxy group —CH(OH)— of the $C_1$–$C_6$-alkyloxy, $C_1$–$C_4$-alkyloxy-$C_1$–$C_4$-alkyloxy, hydroxy-$C_1$–$C_4$-alkyloxy, $C_1$–$C_6$-alkanoyloxy, tris-($C_1$–$C_4$-alkyl)-silyloxy or hydroxy group is optionally substituted by a keto grouping —C(=O)— or keto grouping protected in the form of a ketal, thioketal, cyanhydrin, cyanosilyl ether or a germinal hydroxyethinyl group;

n is 1 or 2;

R1 is α-methyl, β-methyl, α-ethyl, β-ethyl or H;

each sulfamoyloxy group —$OSO_2NHR_2$ is attached at a point selected from the group consisting of C atoms 1, 2, 3, 4, 6, 7, 11, 15, 16 and 17 and groups R4 and R5 with the proviso that the sulfamoyloxy group is not attached at the C atom 3 when m is 1;

R2 is H,-$C_1$–$C_5$-alkyl, $C_1$–$C_3$-alkyl with annelated saturated ring, aryl-$C_1$–$C_3$-alkyl, $C_1$–$C_5$-alkanoyl, or $C_3$–$C_7$-cycloalkylcarbonyl;

R3 is H, OH, halogen, pseudohalogen, $C_1$–$C_3$-alkyl, $C_3$–$C_7$-cycloalkyl, $1^1,1^1$-cycloalkyl or aryl $C_1$–$C_3$-alkyl;

R4 is H, aryl or $C_1$–$C_{12}$-alkyl;

R5 is H, $C_1$–$C_{12}$-alkyl or $C_1$–$C_{12}$-alkylaryl;

R6 is H or halogen; and m is 1 to 5; and optionally further comprising a feature selected from the group consisting of:

a double bond between a pair of C atoms selected from the group consisting of C atoms 9 and 11, C atoms 8 and 9, C atoms 8 and 14, C atoms 6 and 7, and C atoms 7 and 8;

a double bond between a pair of C atoms selected from the group consisting of C atoms 14 and 15 and C atoms 15 and 16 when n is 1;

two double bonds, one between C atoms 8 and 9 and one between C atoms 14 and 15;

two double bonds, one between C atoms 8 and 9 and one between C atoms 7 and 6; and a cyclopropane grouping or epoxide grouping with α- or β-orientation between C atoms 14 and 15 or C atoms 15 and 16;

and with the condition that R3 is not H or OH when m is 1 and the sulfamoyloxy group is bonded to the aromatic A ring;

and with the exception of the compound estra-1,3,5(10)-trien-3,17β-diyl 3,17-diamidosulfonate.

2. The compounds of claim 1, wherein m is 2 to 5 and the double bond between a pair of C atoms is selected from the group consisting of C atoms 9 and 11, C atoms 8 and 9, C atoms 8 and 14, C atoms 14 and 15, C atoms 6 and 7, and C atoms 7 and 8.

3. The compounds of claim 1, wherein:

R1 is α-methyl, β-methyl, β-ethyl or H;

R2 is H, $C_1$–$C_5$-alkyl, $C_1$–$C_3$-alkyl with annelated saturated ring or aryl-$C_1$–$C_3$-alkyl;

R3 is H or halogen;

R4 is aryl or $C_1$–$C_{12}$-alkyl;

R5 is $C_1$–$C_{12}$-alkyl;

R6 is halogen;

the double bond between a pair of C atoms is selected from the group consisting of C atoms 9 and 11, C atoms 8 and 9, C atoms 8 and 14, C atoms 14 and 15, C atoms 6 and 7, and C atoms 7 and 8; and the cyclopropane grouping or epoxide grouping with α- or β-orientation is between C atoms 14 and 15.

4. The compounds of claim 1, wherein:

R1 is α-methyl, β-methyl, α-ethyl or β-ethyl;

each sulfamoyloxy group —$OSO_2NHR_2$ is attached at a point selected from the group consisting of C atoms 7, 11, 15, 16 and 17, an aryl group R4 and the aromatic A ring;

R2 is H, $C_1$–$C_5$-alkyl, $C_1$–$C_5$-alkanoyl, or $C_3$–$C_7$-cycloalkylcarbonyl;

R3 is H, OH, chlorine, bromine, fluorine, $N_3$, CN, SCN or SeCN;

R6 is H chlorine, bromine or fluorine; and m is 1 or 2.

5. The compounds of claim 1, wherein:

R1 is β-methyl or β-ethyl;

R2 is H, $C_1$–$C_5$-alkyl, $C_1$–$C_3$-alkyl with annelated saturated ring or aryl-$C_1$–$C_3$-alkyl;

R3 is bromine, $^{76}$Br, fluorine, $^{18}$F, $^{125}$I, $^{131}$I or astatine;

R4 is aryl or $C_1$–$C_{12}$-alkyl;

R5 is $C_1$–$C_{12}$-alkyl;

R6 is bromine, $^{76}$Br, fluorine, or $^{18}$F;

m is 1 to 2;

a first sulfamoyloxy grouping is attached at the aromatic A ring; and when m=2, a second sulfamoyloxy group is attached at C atom 17 in an α- or β-position.

6. A compound having formula I according to claim 1 selected from the group consisting of:

3,17β-disulfamoyloxy-13β-methyl-D-homo-1,3,5(10)-gonatriene, 3,17β-disulfamoyloxy-13β-methyl-8α-D-homo-1,3,5(10)-gonatriene, 3,17β-disulfamoyloxy-13β-ethyl-1,3,5(10)-gonatriene, 3,17β-disulfamoyloxy-13β-methyl-1,3,5(10),7(8)-gonatetraene, 3,17β-disulfamoyloxy-13β-methyl-1,3,5(10)8,6-gonapentaene, 3,17β-disulfamoyloxy-13β-methyl-1,3,5(10),8-gonatetraene, 3,17β-disulfamoyloxy-13β-methyl-1,3,5(10),8,14-gonapentaene, 3,17β-disulfamoyloxy-13β-methyl-1,3,5(10),8(14)-gonatetraene, 3,17β-disulfamoyloxy-13β-methyl-1,3,5(10),9(11)-gonatetraene, 3,17β-disulfamoyloxy-13β-ethyl-1,3,5(10),9(11)-gonatetraene, 3,17β-disulfamoyloxy-14β-15β-methylene-13β-methyl-1,3,5(10),8-gonatetraene, 3,17α-disulfamoyloxy-14β-15β-methylene-13β-methyl-1,3,5(10),8-gonatetraene, 3,17β-disulfamoyloxy-14α-15α-methylene-13β-methyl-1,3,5(10),8-gonatetraene, 3,17α-disulfamoyloxy-14α-15α-methylene-13β-methyl-1,3,5(10),8-gonatetraene, 16α-bromo-3,17β-disulfamoyloxy-13β-methyl-1,3,5(10)-gonatriene, 16α-bromo-3,1β-disulfamoyloxy-13β-ethyl-1,3,5(10)-gonatriene, 16β-bromo-3,17β-disulfamoyloxy-13β-methyl-1,3,5(10)-gonatriene, 16α-chloro-3,17β-disulfamoyloxy-13β-methyl-1,3,5(10)-gonatriene, 16α-chloro-3,17β-disulfamoyloxy-13β-ethyl-1,3,5(10)-gonatriene, 16β-chloro-3,17β-disulfamoyloxy-13β-methyl-1,3,5(10)-gonatriene, 3,17β-disulfamoyloxy-16α-fluoro-13β-methyl-1,3,5(10)-gonatriene, 3,17β-disulfamoyloxy-16α-fluoro-13β-ethyl-1,3,5(10)-gonatriene, 17β-sulfamoyloxy-13β-methyl-1,3,5(10)-gonatrien-3-ol, 3,16α,17β-trisulfamoyloxy-13β-methyl-1,3,5(10)-gonatriene, 3,17α-disulfamoyloxy-13β-methyl-1,3,5(10)-gonatriene, 17α-sulfamoyloxy-13β-methyl-1,3,5(10)-gonatrien-3-ol, 16α-fluoro-17β-sulfamoyloxy-13β-methyl-1,3,5(10)-gonatrien-3-ol, 16α-bromo-17β-sulfamoyloxy-13β-methyl-1,3,5(10)-gonatrien-3-ol, 17β-sulfamoyloxy-13β-ethyl-1,3,5(10)-gonatrien-3-ol, 3-methoxy-17β-sulfamoyloxy-13β-methyl-1,3,5(10)-gonatriene, and 3-methoxy-17β-sulfamoyloxy-13β-ethyl-1,3,5(10)-gonatriene.

7. Pharmaceutical preparation containing at least one compound having formula I according to claim 1 and a pharmaceutically acceptable carrier.

8. An improved method of treating a subject with a known dose of a sulfatase inhibitor, wherein the improvement comprises:

a) providing steroids of the gonane type or D-homogonane type or salts thereof, having the general formula I;

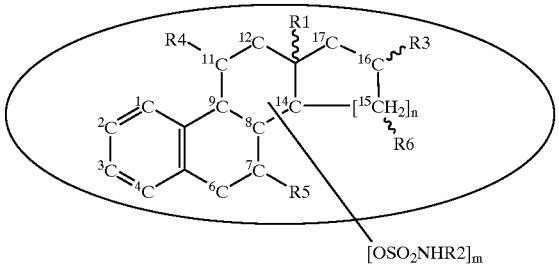

wherein

C atoms 2, 3, 4, 6, 7, 11, 12, 15, 16 and 17 are each independently unsubstituted or substituted by $C_1$–$C_6$-alkyloxy, $C_1$–$C_4$-alkyloxy-$C_1$–$C_4$-alkyloxy, hydroxy-$C_1$–$C_4$-alkyloxy, $C_1$–$C_6$-alkanoyloxy, tris-($C_1$–$C_4$-alkyl)-silyloxy or hydroxy, wherein each secondary hydroxy group —CH(OH)— of the $C_1$–$C_6$-alkyloxy, $C_1$–$C_4$-alkyloxy-$C_1$–$C_4$-alkyloxy, hydroxy-$C_1$–$C_4$-alkyloxy, $C_1$–$C_6$-alkanoyloxy, tris-C1–C4-alkyl)-silyloxy or hydroxy group is optionally substituted by a keto grouping —C(=O)— or a keto grouping protected in the formn of a ketal, thioketal, cyanhydrin, cyanosilyl ether or a geminal hydroxyethinyl group;

n is 1 or 2;

R1 is α-methyl, β-methyl, α-ethyl, β-ethyl or H;

each sulfamoyloxy group —$OSO_2NHR_2$ is attached at a point selected from the group consisting of C atoms 1, 2, 3, 4, 6, 7, 11, 15, 16 and 17 and groups R4 and R5 with the proviso that the sulfamoyloxy group is not attached at the C atom 3 when m is 1;

R2 is H, $C_1$–$C_5$-alkyl, $C_1$–$C_3$-alkyl with annelated saturated ring, aryl-$C_1$–$C_3$-alkyl, $C_1$–$C_5$-alkanoyl, or $C_3$–$C_7$-cycloalkylcarbonyl;

R3 is H, OH, halogen, pseudohalogen, $C_1$–$C_3$ alkyl, $C_3$–$C_7$-cycloalkyl, $1^1,1^1$-cycloalkyl or aryl-$C_1$–$C_3$-alkyl;

R4 is H, aryl or $C_1$–$C_{12}$-alkyl;
R5 is H, $C_1$–$C_{12}$-alkyl or $C_1$–$C_{12}$-alkylaryl;
R6 is H or halogen; and
m is 1 to 5; and optionally further comprising a feature selected from the group consisting of:

a double bond between a pair of C atoms selected from the group consisting of C atoms 9 and 11, C atoms 8 and 9, C atoms 8 and 14, C atoms 6 and 7, and C atoms 7 and 8;

a double bond between a pair of C atoms selected from the group consisting of C atoms 14 and 15 and C atoms 15 and 16 when n is 1;

two double bonds one between C atoms 8 and 9 and one between C atoms 14 and 15;

two double bonds, one between C atoms 8 and 9 and one between C atoms 7 and 6; and a cyclopropane grouping or epoxide grouping with (α- or β-orientation between C atoms 14 and 15 or C atoms 15 and 16;

and with the condition that R3 is not H or OH when m is 1 and the sulfamoyloxy group is bonded to the aromatic A ring;

and with the exception of the compound estra-1,3,5(10)-trien-3, 17β-diyl 3,17-diamidosulfonate;

b) determining the equivalent dose of the compound according to formula I for the known dose of the sulfatase inhibitor; and c) substituting the compound for the sulfatase inhibitor in the method of treating the subject.

9. An improved diagnostic method using a known dose of a sulfatase inhibitor, wherein the improvement comprises:

a) providing steroids of the gonane type or D-homo-gonane type or salts thereof, having the general formula I:

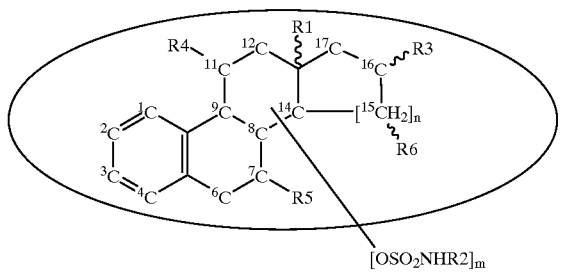

I wherein
C atoms 2, 3, 4, 6, 7, 11, 12, 15, 16 and 17 are each independently unsubstituted or substituted by $C_1$–$C_6$-alkyloxy, $C_1$–$C_4$-alkyloxy-$C_1$–$C_4$-alkyloxy, hydroxy-$C_1$–$C_4$-alkyloxy, $C_1$–$C_6$-alkanoyloxy, tris-($C_1$–$C_4$-alkyl)-silyloxy or hydroxy, wherein each secondary hydroxy group —CH(OH)— of the $C_1$–$C_6$-alkyloxy, ($C_1$–$C_4$-alkyloxy-$C_1$–$C_4$-alkyloxy, hydorxy-$C_1$–$C_4$-alkyloxy, $C_1$–$C_6$-alkanoyloxy, tris-($C_1$–$C_4$-alkyl)-silyloxy or hydroxy group is optionally substituted by a keto grouping —C(=O)— or a keto grouping protected in the form of a ketal, thioketal, cyanhydrin, cyanosilyl ether or a geminal hydroxyethinyl group;

n is 1 or 2;

R1 is α-methyl, β-methyl, α-ethyl, β-ethyl or H;

each sulfamoyloxy group —$OSO_2NHR_2$ is attached at a point selected from the group consisting of C atoms 1, 2, 3, 4, 6, 7, 11, 15, 16 and 17 and groups R4 and R5 with the proviso that the sulfamoyloxy group is not attached at the C atom 3 when m is 1;

R2 is H, $C_1$–$C_5$-alkyl, $C_1$–$C_3$-alkyl with annelated saturated ring, aryl-$C_1$–$C_3$-alkyl, $C_1$–$C_5$-alkanoyl, or $C_3$–$C_7$-cycloalkylcarbonyl;

R3 is H, OH, halogen, pseudohalogen, $C_1$–$C_3$ alkyl, $C_3$–$C_7$-cycloalkyl, $1^1,1^1$-cycloalkyl or aryl-$C_1$–$C_3$-alkyl;

R4 is H, aryl or $C_1$–$C_{12}$-alkyl;
R5 is H, $C_1$–$C_{12}$-alkyl or $C_1$–$C_{12}$-alkylaryl;
R6 is H or halogen; and
m is 1 to 5; and optionally further comprising a feature selected from the group consisting of:

a double bond between a pair of C atoms selected from the group consisting of C atoms 9 and 11, C atoms 8 and 9, C atoms 8 and 14, C atoms 6 and 7, and C atoms 7 and 8;

a double bond between a pair of C atoms selected from the group consisting of C atoms 14 and 15 and C atoms 15 and 16 when n is 1;

two double bonds, one between C atoms 8 and 9 and one between C atoms 14 and 15;

two double bonds, one between C atoms 8 and 9 and one between C atoms 7 and 6; and a cyclopropane grouping or epoxide grouping with α- or β-orientation between C atoms 14 and 15 or C atoms 15 and 16;

and with the condition that R3 is not H or OH when m is 1 and the sulfamoyloxy group is bonded to the aromatic A ring;

and with the exception of the compound estra-1,3,5(10)-trien-3,17β-diyl 3,17-diamidosulfonate;

b) determining the equivalent dose of the compound according to formula I for the known dose of the sulfatase inhibitor; and c) substituting the compound for the sulfatase inhibitor in the diagnostic method.

* * * * *